United States Patent
Feng et al.

(10) Patent No.: US 11,213,475 B2
(45) Date of Patent: Jan. 4, 2022

(54) MULTI-LAYER PEELABLE NAIL POLISH

(71) Applicant: L'ORÉAL, Paris (FR)

(72) Inventors: Jianxin Feng, Clark, NJ (US); Ramakrishnan Hariharan, Springfiel, NJ (US)

(73) Assignee: L'ORÉAL, Paris (FR)

( * ) Notice: Subject to any disclaimer, the term of this patent is extended or adjusted under 35 U.S.C. 154(b) by 385 days.

(21) Appl. No.: 16/369,088

(22) Filed: Mar. 29, 2019

(65) Prior Publication Data

US 2020/0306166 A1 Oct. 1, 2020

(51) Int. Cl.
*A61K 8/81* (2006.01)
*A61Q 3/02* (2006.01)
*A61K 8/73* (2006.01)

(52) U.S. Cl.
CPC .............. *A61K 8/817* (2013.01); *A61K 8/731* (2013.01); *A61Q 3/02* (2013.01); *A61K 2800/884* (2013.01)

(58) Field of Classification Search
None
See application file for complete search history.

(56) References Cited

U.S. PATENT DOCUMENTS

| 9,827,184 B2 | 11/2017 | Zhao |
| 2017/0065512 A1 | 3/2017 | Zhu et al. |

FOREIGN PATENT DOCUMENTS

| CN | 104027261 A | 9/2014 |
| CN | 105496817 A | 4/2016 |
| CN | 105534741 B | 5/2016 |
| CN | 108025192 A | 5/2018 |
| WO | 2014135659 A2 | 9/2014 |

*Primary Examiner* — Nicole P Babson
(74) *Attorney, Agent, or Firm* — Meagher Emanuel Laks Goldberg & Liao, LLP

(57) ABSTRACT

A method and system for a multi-layer peelable nail cosmetic compositions are disclosed. The multi-layer system includes a water-washable, non-UV curable nail basecoat composition in a hand-held, non-pressurized container. The basecoat composition includes a hydrophilic poly(N-vinyl) lactam polymer, at least one alcohol, and at least one plasticizer. The multi-layer system also includes a colored non-UV curable nail colorcoat composition that includes a primary film former, a secondary film former, a plasticizer, and a colorant.

20 Claims, No Drawings

MULTI-LAYER PEELABLE NAIL POLISH

FIELD OF THE INVENTION

The present invention relates to nail enamel compositions, and specifically to fast-drying nail enamel compositions comprising two different resins.

BACKGROUND

Consumers use nail enamel to cosmetically enhance the appearance of their nails or protect the nails from the abuses found in their everyday environment. Nail enamels are typically formulated to dry rapidly while providing provide good shine and high durability, and ideally allow the incorporation of an appearance-enhancing material such as a pearlescent or glitter. However, removal of such nail enamels often requires particular solvents in order to remove the enamel, which can potentially damage the nail plate.

Peel-off nail polishes are always attractive to the customers who have big concerns on the potential damages of polish removers to nail plates. Since no solvents are usually required for their removal, peel-off nail polishes are usually considered healthier and more environmentally friendly than other types.

Current peel-off products are either water-based or UV-curable. Although water-based nail polishes are solvent-free and thus are safer to use and easier to remove, they tend to have slower drying speeds and compromised wear characteristics, and some have stability issues when incorporating a pearlescent or glitter. Conversely, UV-curable products often have rapid drying, good shine, and high durability, but the nail plate surfaces could be defatted and damaged during peeling due to the strong adhesion of the coating layers. Additionally, the use of glitters in the UV systems could be limited since they may prevent the penetration of UV lights into the bottom layer of the coats.

A peelable nail product that provides comparable benefits to traditional nail enamels is therefore desirable.

BRIEF SUMMARY

In a first aspect, the present invention is directed to a water-washable, non-UV curable nail basecoat composition in a hand-held, non-pressurized container. The composition includes a hydrophilic poly(N-vinyl)lactam polymer, such as a lactam of caproic acid (e.g., Vinyl Caprolactam/VP/Dimethylaminoethyl methacrylate copolymer), at least one alcohol, and at least one plasticizer. The hydrophilic poly(N-vinyl)lactam polymer may include lactam polymers and copolymers thereof. The hydrophilic poly(N-vinyl)lactam polymer may be present in the composition in a total amount between 7% and 40% by weight. The composition may include water, although if present, it is preferably in a total amount of less than 10% by weight. The composition may include two or more alcohols, each having a boiling point less than the boiling point of water. The composition may consist of, or consist essentially of, a hydrophilic poly(N-vinyl)lactam polymer, at least one alcohol, and at least one plasticizer. For example, the composition may consist of a hydrophilic poly(N-vinyl)lactam polymer, two or more alcohols, and two or more plasticizer (e.g., sucrose acetate isobutyrate and dipropylene glycol dibenzoate).

In a second aspect, a kit is provided. The kit includes the above-described water-washable, non-UV curable nail basecoat composition in a hand-held, non-pressurized container, as well as a colored non-UV curable nail colorcoat composition. The colorcoat may comprise a primary film former (including a cellulose derivative, such as cellulose acetate butyrate), a secondary film former, a plasticizer, and a colorant.

In a third aspect, a multi-layer nail composition is disclosed, containing at least two layers. A first layer is generated on a natural or synthetic nail, the first layer being the water-washable, non-UV curable nail basecoat composition described above. On top of that first layer, a second layer is added, where the second layer is a colored non-UV curable nail colorcoat composition, such as the one in the kit described above.

In a fourth aspect, a method of making up natural or synthetic nails is provided. The method includes applying onto the nails the above-described water-washable, non-UV curable nail basecoat composition in a hand-held, non-pressurized container. The composition may be brushed on a fingernail or toenail. The method may continue by applying onto the nails a colored non-UV curable nail colorcoat composition (such as the composition described above) over the water-washable, non-UV curable nail basecoat composition. The method may continue by peeling off the colored non-UV curable nail colorcoat composition. The method may continue by removing the water-washable, non-UV curable nail basecoat composition utilizing a liquid including water.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "include", "includes" and "including" are meant to be non-limiting.

As used herein, the term "non-pressurized container" indicates a container whose internal contents are at a pressure at approximately atmospheric pressure, typically within ±5% of standard atmospheric pressure (14.7 psia). For example, in some embodiments, a non-pressurized container is a container at a pressure corresponding to ambient atmospheric pressure in the container of not more than 105 kPa absolute (15.22 psia).

The present invention is directed to a water-washable, non-UV curable nail basecoat composition in a hand-held, non-pressurized container. Typically, the container will be glass, and will contain an applicator (such as a brush) for applying the composition to nails, including natural or synthetic nails.

The composition should comprise three basic components: (1) a hydrophilic poly(N-vinyl)lactam polymer, (2) at least one alcohol, and (3) at least one plasticizer.

The hydrophilic poly(N-vinyl) lactam polymer includes, but is not limited to, those polymers comprising a lactam having between 3 and 7 ring atoms, such as polyvinyl pyrrolidone (PVP) and poly(N-vinylcaprolactam) (PVC), including copolymers and blends thereof. In certain embodiments, the hydrophilic poly(N-vinyl)lactam polymer is Vinyl Caprolactam/VP/Dimethylaminoethyl methacrylate copolymer, which is available under the name ADVANTAGE™ HC 37 from Ashland.

The molecular weight of the hydrophilic poly(N-vinyl) lactam polymer is not critical; however, the weight average molecular weight of the hydrophilic poly(N-vinyl) lactam polymer is generally in the range of approximately 100,000 to 2,000,000, more typically in the range of approximately 500,000 to 1,500,000.

The hydrophilic poly(N-vinyl)lactam polymer is typically present in the composition in a total amount less than 40% by weight, such as between 7% and 40% by weight, between 7% and 25% by weight, or between 10% and 20% by weight.

The at least one alcohol includes, but is not limited to, alcohols having a boiling point less than the boiling point of water, and/or alcohols having a $C_1$-$C_4$ alkyl group. For example, in some embodiments, the at least one alcohol includes ethyl alcohol and/or isopropyl alcohol. In some embodiments, the at least one alcohol includes at least two alcohols, each having a boiling point less than the boiling point of water and/or having a $C_1$-$C_4$ alkyl group.

The at least one alcohol may be present in the composition in a total amount of at least 30% by weight, such as between 30% and 80% by weight.

The at least one plasticizer may include, but is not limited to, esters of saccharide and of a carboxylic acid, such as $C_1$-$C_6$ acid esters of sucrose, glycols and their derivatives, or benzoic acid derivatives. Non-limiting examples of a C1-C6 acid esters of sucrose that may be used according to various embodiments include sucrose acetate isobutyrate available under the name SAIB-100® from Eastman. Non-limiting examples of glycols and their derivatives include glycol ethers (such as ethylene glycol, propylene glycol, diethylene glycol ethyl ether, diethylene glycol methyl ether, diethylene glycol butyl ether, diethylene glycol hexyl ether, diethylene glycol dibutyl ether, ethylene glycol methyl ether, ethylene glycol ethyl ether, ethylene glycol butyl ether, and ethylene glycol hexyl ether); glycol esters (such as diethylene glycol butyl ether acetate, propylene glycol dibenzoate and dipropylene glycol dibenzoate); and propylene glycol derivatives (such as propylene glycol phenyl ether, propylene glycol diacetate, dipropylene glycol butyl ether, tripropylene glycol butyl ether, propylene glycol methyl ether, dipropylene glycol ethyl ether, tripropylene glycolmethyl ether and diethylene glycol methyl ether, and propylene glycolbutyl ether). Non-limiting examples of a benzoic acid derivative include diethylene glycol dibenzoate, dipropylene glycol dibenzoate, and 1,2-propylene glycol dibenzoate.

The at least one plasticizer may include two or more plasticizers.

The at least one plasticizer may be present in an amount ranging from about 1% to about 20% by weight, more preferably from about 5% to about 18% by weight, and still more preferably from about 8% to about 16% by weight.

In certain embodiments, the water-washable, non-UV curable nail basecoat composition may consist of, or consist essentially of, a hydrophilic poly(N-vinyl)lactam polymer, at least one alcohol, and at least one plasticizer. In these embodiments, any additional ingredient would not impact the removability of the composition.

In certain embodiments, the composition may include a small amount of water. In those embodiments, the composition may include less than 10% water, by weight, and may include less than 5% water by weight.

The composition may optionally contain an adjuvant, such as a preserving agent, antioxidant, fragrance, conditioning agent, sequestrant (such as EDTA), or dyestuff. The amounts of these various adjuvants are those conventionally used in the field under consideration, for example from 0.01% to 10% by weight and preferably from 0.01% to 5% by weight, relative to the total weight of the cosmetic.

In certain embodiments, a kit may be provided. The kit will typically contain the water-washable, non-UV curable nail basecoat composition as disclosed above, as well as a colored non-UV curable nail colorcoat composition.

The colored non-UV curable nail colorcoat composition may include a primary film former, a secondary film former, a plasticizer, and a colorant.

One or more primary film formers may be present in the colorcoat composition. In certain embodiments, the primary film former may include a nitrocellulose or a cellulose derivative. The cellulose derivative may be a cellulose ester. Non-limiting examples of suitable primary film formers includes nitrocellulose, methyl cellulose, ethyl cellulose, propyl cellulose, butyl cellulose, cellulose phthalate, cellulose acetate propionate, cellulose acetate butyrate, cellulose acetate, hydroxyethyl cellulose, ethylhydroxyethyl cellulose, hydroxypropyl cellulose, and the like. These primary film formers may be present in a total amount of between 5% and 30% by weight.

One or more secondary film formers may be present in the colorcoat composition. In certain embodiments, the secondary film former may include epoxy resins, (meth)acrylate homopolymers and copolymers, polyurethanes, polyacryls, polymethacryls, cellulosic polymers, styrene-acryl copolymers, polystyrene-polyacryl mixtures, polysiloxanes, polyethers, polyesters, urethane-acryl copolymers, cellulose acetate propionate, siloxane-urethane copolymers, polyurethane-polymethacryl mixtures, silicone-acryl copolymers, vinyl acetate polymers, and mixtures thereof. Specific examples of suitable secondary film forming agents include, but are not limited to acrylates copolymer, phthalic anhydride/glycerin/glycidyl decanoate copolymer, adipic acid/neopentyl glycol/trimellitic anhydride copolymer, tosylamide/epoxy resin, butyl acetate (and) acrylates copolymer, and hydrogenated acetophenone/oxymethylene copolymer.

In certain embodiments, the secondary film former may be a polymer comprising repeating units of at least one (meth)acrylate unit and vinyl copolymers. Potential acrylates copolymers include, but are not limited to, those sold under the PECOREZ® name such as, for example, PECOREZ AC 50.

These secondary film formers may be present in a total amount of between 1% and 10% by weight.

One or more plasticizers may be present in the colorcoat composition. The plasticizer may be a citric acid derivative, such as an optionally hydroxylated triester of a $C_2$-$C_8$ tricarboxylic acid and of a $C_2$-$C_8$ alcohol, such as trioctyl citrate, triethyl citrate, acetyl tributyl citrate, tributyl citrate or acetyl tributyl citrate. These plasticizers may be present in a total amount of between 1% and 10% by weight.

The colorcoat composition may contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in embodiments of the disclosed compositions will depend on the color, intensity and use of the cosmetic composition and, as a result, will be determined by those skilled in the art of cosmetic formulation. However, one preferred amount of colorant for use in the present invention is from about 0.5% to about 7.5%, based on the weight of the composition.

The colorcoat composition may optionally contain solvents, including but not limited to short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate. The solvents film formers may be present in a total amount of between 1% and 60% by weight, such as between 30% and 60% by weight.

The colorcoat composition may optionally contain an adjuvant, such as a preserving agent, thickening agents, antioxidant, fragrance, or sequestrant (such as EDTA). The amounts of these various adjuvants are those conventionally used in the field under consideration, for example from 0.01% to 15% by weight and preferably from 0.01% to 5% by weight, relative to the total weight of the cosmetic.

In use, the water-washable, non-UV curable nail basecoat and the colored non-UV curable nail colorcoat composition form a multi-layer nail composition. Starting with a natural or synthetic nail (including human fingernails, human toenails, etc.), a water-washable, non-UV curable nail basecoat as described above is applied to the natural or synthetic nail, forming a first layer in contact with, and on top of, the natural or synthetic nail. Optionally, this first layer may be brushed on.

On top of this first layer, a colored non-UV curable nail colorcoat composition as described above is applied, forming a second layer in contact with, and on top of, the first layer. Preferably, the colorcoat composition is applied after the basecoat has fully dried. Optionally, this second layer may be brushed on. Preferably, this multi-layer nail composition is then allowed to dry. Optionally, an additional layer, such as a clear topcoat, may be applied on top of the second layer.

At some point after the second layer is applied, the second layer (and third layer, if present) may be peeled off. This may be done by lifting using fingers or tools, scraping the second layer (and third layer, if present) with a hard material (such as another fingernail or tool), or scrubbing or rubbing the second layer off.

After peeling off the second layer, the water-washable, non-UV curable nail basecoat composition may be removed, utilizing a liquid comprising water. The liquid comprising water may be a liquid well known to those of skill in the art and includes, but is not limited to, water, water with soap, and an aqueous cleaning solution. In preferred embodiments, the liquid is water.

Example—Base Coat

| Material | % By Weight |
| --- | --- |
| Vinyl Caprolactam/VP/Dimethylaminoethyl methacrylate copolymer | 15-25% |
| Ethanol | 25-40% |
| Isopropyl Alcohol | 25-50% |
| Sucrose Acetate Isobutyrate | 5-10% |
| Dipropylene Glycol Dibenzoate | 1-5% |

All materials are added at room temperature and mixed at high speed until uniform.

Example—Color Coat

| Material | % By Weight |
| --- | --- |
| Primary Film Former | 20-30% |
| Secondary Film Formers | 5-10% |
| Plasticizers | 5-10% |
| Solvents | 30-60% |
| Colorants | 1-10% |

All materials, excluding the colorants, are added at room temperature. The batches were then mixed until homogenous, then the pigments were added, and the mixing speed was increased until homogenous.

Those skilled in the art will recognize or be able to ascertain using no more than routine experimentation many equivalents to the specific embodiments of the invention described herein. Such equivalents are intended to be encompassed by the following claims.

What is claimed is:

1. A water-washable, non-UV curable nail basecoat composition in a hand-held, non-pressurized container, the composition comprising:
   a hydrophilic poly(N-vinyl)lactam polymer;
   at least one alcohol; and
   at least one plasticizer.

2. The water-washable, non-UV curable nail basecoat composition according to claim 1, wherein the hydrophilic poly(N-vinyl)lactam polymer includes a lactam of caproic acid.

3. The water-washable, non-UV curable nail basecoat composition according to claim 1, wherein the hydrophilic poly(N-vinyl)lactam polymer is Vinyl Caprolactam/VP/Dimethylaminoethyl methacrylate copolymer.

4. The water-washable, non-UV curable nail basecoat composition according to claim 1, wherein the hydrophilic poly(N-vinyl)lactam polymer is present in the composition in a total amount between 7% and 40% by weight.

5. The water-washable, non-UV curable nail basecoat composition according to claim 1, further comprising water, wherein the water is present in the composition in a total amount less than 10% by weight.

6. The water-washable, non-UV curable nail basecoat composition according to claim 1, wherein the at least one alcohol includes at least two alcohols, each having a boiling point less than the boiling point of water.

7. The water-washable, non-UV curable nail basecoat composition according to claim 1, wherein the composition consists of:
a hydrophilic poly(N-vinyl)lactam polymer;
at least one alcohol; and
at least one plasticizer.

8. The water-washable, non-UV curable nail basecoat composition according to claim 7, wherein the at least one plasticizer includes two or more plasticizers.

9. The water-washable, non-UV curable nail basecoat composition according to claim 7, wherein the at least one plasticizer is selected from the group consisting of sucrose acetate isobutyrate and dipropylene glycol dibenzoate.

10. A kit, comprising:
the water-washable, non-UV curable nail basecoat composition according to claim 1; and
a colored non-UV curable nail colorcoat composition comprising a primary film former, a secondary film former, a plasticizer, and a colorant.

11. The kit according to claim 10, wherein the primary film former is a cellulose derivative.

12. The kit according to claim 11, wherein the primary film former is cellulose acetate butyrate.

13. A multi-layer nail composition, comprising:
a first layer comprising the water-washable, non-UV curable nail basecoat composition according to claim 1, the first layer in contact with a natural or synthetic nail; and
a second layer comprising a colored non-UV curable nail colorcoat composition comprising a primary film former, a secondary film former, a plasticizer, and a colorant, the second layer being in contact with the first layer.

14. A method of making up natural or synthetic nails comprising the steps of:
applying onto the nails a water-washable, non-UV curable nail basecoat composition from a hand-held, non-pressurized container, the composition comprising a hydrophilic poly(N-vinyl)lactam polymer, a plasticizer, and at least one alcohol.

15. The method according to claim 14, wherein the hydrophilic poly(N-vinyl)lactam polymer includes a lactam of caproic acid, and wherein the water-washable, non-UV curable nail basecoat composition includes at least two plasticizers and at least two alcohols.

16. The method according to claim 14, wherein the hydrophilic poly(N-vinyl)lactam polymer is present in the composition in a total amount between 7% and 40% by weight, and
wherein the water-washable, non-UV curable nail basecoat composition includes between 0% and 10% by weight of water.

17. The method according to claim 14, wherein the water-washable, non-UV curable nail basecoat composition is brushed onto a fingernail or toenail.

18. The method according to claim 14, further comprising applying onto the nails a colored non-UV curable nail colorcoat composition over the water-washable, non-UV curable nail basecoat composition, the colored non-UV curable nail colorcoat composition comprising a primary film former, a secondary film former, a plasticizer, and a colorant.

19. The method according to claim 18, further comprising peeling off the colored non-UV curable nail colorcoat composition.

20. The method according to claim 19, further comprising removing the water-washable, non-UV curable nail basecoat composition, after peeling off the colored non-UV curable nail colorcoat composition, utilizing a liquid comprising water.

* * * * *